(12) United States Patent
Sun

(10) Patent No.: US 7,115,794 B2
(45) Date of Patent: Oct. 3, 2006

(54) METHOD FOR DIRECT NUCLEIC ACID UPTAKE

(75) Inventor: Piera S. Sun, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 1 day.

(21) Appl. No.: 10/849,082

(22) Filed: May 19, 2004

(65) Prior Publication Data

US 2004/0250308 A1 Dec. 9, 2004

Related U.S. Application Data

(60) Provisional application No. 60/471,611, filed on May 19, 2003.

(51) Int. Cl.
*A01K 67/00* (2006.01)
(52) U.S. Cl. ....................................................... 800/13
(58) Field of Classification Search .................. 800/13
See application file for complete search history.

(56) References Cited

OTHER PUBLICATIONS

Godbey WT, Poly(ethylenimine) and its role in gene delivery, 1999, J. of Controlled Release, vol. 60, pp. 149-160.*
Tseng FS, Introducing foreign DNA into tiger shrimp (*Penaeus monodon*) by electroporation, 2000, Theriogenology, vol. 54, pp. 1421-1432.*
Mengerink KJ, Glycobiology of sperm-egg interactions in deuterostomes, 2001, Glycobiology, vol. 11, pp. 37R-43R.*
Mozino NM, Distribution of lectin binding sites in *Xenopous laevis* egg jelly, 1999, Developmental Biology, vol. 210, pp. 428-439.*
Liu C, Targeted disruption of the mZP3 gene results in production of eggs lacking in zona pellucida and infertility in female mice, 1996, PNAS, vol. 93, pp. 5431-5436.*
Ahn et al., "Biodegradable Poly(Ethylenimine) for Plasmid DNA Delivery," *J. of Controlled Release* 80:273-282 (2002).
Arenal et al., "Gene Transfer in Shrimp (*Litopenaeus schmitti*) by Electroporation of Single-Cell Embryos and Injection of Naked DNA into Adult Muscle," *Biotecnologia Aplicada* 17:247-250 (2000).
Bachere et al., "Transgenic Crustaceans," *World Aquaculture* 28(4):51-55 (1997).

Boussif et al., "A Versatile Vector for Gene and Oligonucleotide Transfer Into Cell in Culture and In Vivo: Polyethylenimine," *Proc. Natl. Acad. Sci. USA* 92:7297-7301 (1995).
Cadoret et al., "Microinjection of Bivalve Eggs: Application in Genetics," *Mol. Mar. Biol. Biotechnol.* 6:72-77 (1997).
Carballada et al., "Transfection of Mouse Eggs and Embryos Using DNA Combined at Cationic Liposomes," *Mol. Reprod. Dev.* 56:360-365 (2000).
Chong et al., "Expression and Fate of CAT Reporter Gene Microinjected into Fertilized Medaka (*Oryzias latipes*) Eggs in the Form of Plasmid DNA, Recombinant Phage Particles and its DNA," *Theor. Appl. Genet.* 78:369-380 (1989).
Collas et al., "Transferring Foreign Genes into Zebrafish Eggs By Microinjection," In Houdebine, L.M. (ed.) Transgenic Animals-Generation and Use, Harwood Academic Publishers, pp. 119-122 (1997).
Horbinski et al., "Polyethylenimine-Mediated Transfection of Cultured Postmitotic Neurons From Rat Sympathetic Ganglia and Adult Human Retina," *BMC Neuroscience* 2:2, 8 pgs., Feb. 16, 2001.
MacLean et al., "Transgenic Transmission and Expression in Rainbow Trout and Tilapia," *Mol. Mar. Biol. Biotechnol.* 1:355-365 (1992).
Mailhe et al., "Future of Biotechnology-Based Control of Disease in Marine Invertebrates," *Mol. Mar. Biol. Biotechnol.* 4(4):275-283 (1995).
Penman et al., "Factors Effecting Survival and Integration Following Micro-Injection of Novel DNA in Rainbow Trout Eggs," *Aquaculture* 85:35-50 (1990).
Preston et al., "Delivery of DNA to Early Embryos of the Kuruma Prawn, *Peneaus japonicus*," *Aquaculture* 181:225-234 (2000).
Remy et al., "Gene-Transfer with Lipospermines and Polyethylenimines," *Adv. Drug Delivery Rev.* 30:85-95 (1998).
Tseng et al., "Introducing Foreign DNA Into Tiger Shrimp (*Penaeus monodon*) by Electroporation," *Theriogenology* 54:1421-1432 (2000).
Wall, R.J., "New Gene Transfer Methods," *Theriogenology* 57:189-201 (2002).

* cited by examiner

*Primary Examiner*—Dave Trong Nguyen
*Assistant Examiner*—David A. Montanari
(74) *Attorney, Agent, or Firm*—Nixon Peabody LLP

(57) ABSTRACT

The present invention relates to a method of nucleic acid molecule delivery into a fertilized egg. This method involves providing a fertilized egg prior to its formation of a protective layer, providing a nucleic acid molecule, and combining the nucleic acid molecule and the fertilized egg under conditions effective to allow the nucleic acid molecule to be delivered into the egg.

14 Claims, 7 Drawing Sheets

Detection of TSV-CP Expression via RT-PCR

1. Effectene + DNA
2. DNA alone
3. No DNA
4. Effectene alone
5. Positive control
6. Molecular Marker 500 bp
300 bp Assays were performed at day 8 after hatching

FIGURE 6

Expression of TSV-CP

1 Control
2 Superfect/DNA exposure @ 4-10 min. p-sp
3 Superfect/DNA exposure @ 11-16 min. p-sp
4 Superfect/DNA exposure @ 17-22 min. p-sp
5 Lipofectamine2000/DNA @ 4-16 min. p-sp
6 Lipofectamine2000/DNA @ 17-22 min. p-sp
7 DNA alone @ 4-10 min. p-sp
8 DNA alone @ 11-16 min. p-sp
9 DNA alone @ 17-22 min. p-sp
10 DNA alone @ 24 min. p-sp
11 MWM
12 TSV-CP (AS)

FIGURE 7

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:
```

-continued

```
      Oligonucleotide primer

<400> SEQUENCE: 1
cttaattaat gcctgctaac cc                                                  22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 2
attgatgtct gcttagcatt ca                                                  22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
tgatacaaca accagtggag gac                                                 23

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 4
tgtcatcagg tagggaaatt tc                                                  22
```

METHOD FOR DIRECT NUCLEIC ACID UPTAKE

This application claims the benefit of U.S. Provisional Patent Application Ser. No. 60/471,611, filed May 19, 2003, which is hereby incorporated in its entirety.

The subject matter of this application was made with support from NIH NBRS Grant No. 5R25GM56930-05 and Sea Grant No. NA86RG0041 Project No. R/AQ-59, and NIH Grant No. 2T34GM07684-24. The U.S. Government may have certain rights.

FIELD OF THE INVENTION

The present invention provides a simple, efficient method of delivering a nucleic acid molecule into a fertilized egg.

BACKGROUND OF THE INVENTION

Diseases in shrimp aquaculture have substantially reduced production and resulted in significant revenue losses (Lightner et al., "Strategies for the Control of Viral Diseases of Shrimp in the Americas," *Fish Path.* 33:165–180 (1998); Dhar et al., "Isolation of Differentially Expressed Genes in White Spot Virus (WSV) Infected Shrimp (*Penaeus stylirostris*)," In: World Aquaculture Society, France (2000); Brock et al., "Disease Prevention and Control for Gametes and Embryos of Fish and Marine Shrimp," *Aquaculture* 197:137–159 (2001)) The use of molecular biology techniques to produce pathogen-resistant strains of shrimp through genetic transformation technology is considered a highly promising strategy for control of shrimp viral disease (Mialhe et al., "Future of Biotechnology-Based Control of Disease in Marine Invertebrates," *Mol. Mar. Biol. Biotechnol.* 4(4):275–83 (1995); Bachere et al., "Transgenic Crustaceans," *World Aquaculture* 28(4):51–5 (1997)). In the past decade, pathogen-resistant transgenic animals and plants have been developed (Beachy, "Virus Cross-Protection in Transgenic Plants," in D. P. S. Verma, and R. B. Goldberg, (eds.), *Plant Gene Research: Temporal and Spatial Regulation of Plant Genes*, New York: Springer Verlag pp. 313–327 (1998); Kim et al., "Disease Resistance in Tobacco and Tomato Plants Transformed with the Tomato Spotted Wilt Virus Nucleocapsid Gene," *Plant Dis.* 78:615–21 (1993); Sin, F. Y. T., "Transgenic Fish," *Rev. Fish Biol.* 7(4):417–41 (1997)), but use of such technology has only just begun for shrimp research. While methods for detecting viral disease in shrimp, including polymerase chain reaction (Dhar et al., "Detection and Quantification of Infectious Hypodermal and Hematopoietic Necrosis Virus (IHHNV) and White Spot Virus (WSV) of Shrimp by Real-Time Quantitative PCR and SYBR Chemistry," *J. Clin. Microbiol.* 39:2835–2845 (2001); Tang et al., "Detection and Quantification of Infectious Hypodermal and Hematopoietic Necrosis Virus in Penaeid Shrimp by Real-Time PCR," *Dis. Aquat. Org.* 44(2):79–85 (2001)), light microscopy, and transmission electron microscopy (Nunan et al., "Reverse Transcription Polymerase Chain Reaction (RT-PCR) Used for the Detection of Taura Syndrome Virus (TSV) in Experimentally Infected Shrimp," *Dis. Aquatic. Org.* 34:87–91 (1998); Goarant et al., "Arbitrarily Primed PCR to Type *Vibrio* Spp. Pathogenic for Shrimp," *Appl. Environ. Microbiol.* 65(3):1145–1151 (1999); Chen et al., "Establishment of Cell Culture Systems from Penaeid Shrimp and Their Susceptibility to White Spot Disease and Yellow Head Viruses," *Meth. in Cell Sci.* 21:199–206 (1999); Toullec, "Crustacean Primary Cell Culture: a Technical Approach," *Meth. in Cell Sci.* 21:193–8 (1999); Sukhumsirichart et al., "Characterization and PCR Detection of Hepatopancreatic Parvovirus (HPV) from *Penaeus Monodon* in Thailand," *Dis. Aquat. Org.* 38:1–10 (1999), are widely used, methods for controlling viral disease in shrimp are still in development. One of the drawbacks to molecular engineering in shrimp and other crustaceans thus far has been the lack of a procedure to transform eggs or embryos with DNA that is easy, quick, highly efficient, and results in low mortality of eggs/embryos.

Three common methods of vector-expression for foreign nucleic acid delivery are electroporation (Muller et al., "Introducing Foreign Genes Into Fish Eggs With Electroporated Sperm as a Carrier," *Mol. Mar. Biol. Biotechnol.* 1:276–281 (1992); Powers et al., "Electroporation: a Method for Transferring Genes Into the Gametes of Zebra Fish (*Brachydanio rerio*), Channel Catfish (*Ictalurus punctatus*), and Common Carp (*Cyprimus carpio*)," *Mol. Mar. Biol. Biotechnol.* 1:301–308 (1992); Sin et al., "Gene Transfer in Chinook Salmon by Electroporating Sperm in the Presence of PRSV-lacZ DNA," *Aquaculture* 117:57–69 (1993); Powers et al., "Electroporation as an Effective Means of Introducing DNA Into Abalone (*Haliotis rufescens*) Embryos," *Mol. Mar. Biol. Biotechnol.* 4(4):369–375 (1995); Tsai et al., "Sperm as a Carrier to Introduce an Exogenous DNA Fragment Into the Oocyte of Japanese Abalone (*Haliotis divorsicolor suportexta*)," *Transgenic Res.* 6(1):85–95 (1997); Fraga et al., "Introducing Antisense Oligonucleotides into *Paramecium* via Electroporation," *J. Eukaryot. Microbiol.* 45(6):582–8 (1998); Preston et al., "Delivery of DNA to Early Embryos of the Kuruma Prawn, *Penaeus japonicus*," *Aquaculture* 181:225–234 (2000)), ballistic bombardment (Zelenin et al., "The Delivery of Foreign Genes Into Fertilized Eggs Using High-Velocity Microprojectiles," *FEBS Lett.* 287(1–2):118–120 (1991); Akasaka et al., "Introduction of DNA Into Sea Urchin Eggs by Particle Gun," *Mol. Mar. Biol. Biotechnol.* 4(3):255–261 (1995); Gendreau et al., "Transient Expression of a Luciferase Reporter Gene After Ballistic Introduction Into *Artemia Franciscana* (Crustacea) Embryos," *Aquaculture* 133:199–205 (1995); Baum et al., "Improved Ballistic Transient Transformation Conditions for Tomato Fruit Allow Identification of Organ-Specific Contributions of 1-Box and G-Box to the RBCS2 Promoter Activity," *Plant J.* 12(2): 463–9 (1997); Udvardi et al., "Uptake of Exogenous DNA Via the Skin," *J. Mol. Med.* 77(10):744–50 (1999)), and microinjection (Udvardi et al., "Uptake of Exogenous DNA Via the Skin," *J. Mol. Med.* 77(10):744–50 (1999); Penman et al., "Patterns of Transgene Inheritance in Rainbow Trout (*Oncorhynchus Mykiss*)," *Mol Reprod. Dev.* 30:201–206 (1991); Damen et al., "Transcriptional Regulation of Tubulin Gene Expression in Differentiating Trochoblasts During Early Development of *Patella Vulgata*," *Development* 120: 2835–2845 (1994); Gaiano et al., "Highly Efficient Germ-Line Transmission of Proviral Insertions," *Proc. Natl. Acad. Sci. USA* 93:7777–7782 (1996); Cadoret et al., "Microinjection of Bivalve Eggs: Application in Genetics," *Mol. Mar. Biol. Biotechnol.* 6(1):7277 (1997); Li et al., "Transfer of Foreign Gene to Giant Freshwater Prawn (*Macrobrachium rosenbergii*) by Spermatophore-Microinjection," *Mol. Reprod. Dev.* 56(2): 149–54 (2000)). Among these three methods, microinjection is considered to be the most tedious, but most efficient, method for transferring foreign nucleic acid into marine and fresh water species. It allows precision in delivery of exogenous nucleic acid and increases the chances that a treated egg will be transformed. The introduced nucleic acid is ultimately integrated into the chromosomes of the microinjected organism. Preston et al., "Delivery of DNA to Early Embryos of the Kuruma Prawn, *Penaeus japonicus,*" *Aquaculture* 181:225–234 (2000), examined the relative efficiency of microinjection, electroporation, and particle bombardment for introducing nucleic acid into the embryos of the Kuruma prawn, *Litopenaeus japonicus* and found that microinjection is the most reliable technique but very time consuming. Electroporation is a desirable method for large scale gene transfer, however, host mortality tends to be high. An alternative non-surgical technique (e.g., spermatophore-microinjection), can be used as the delivery system, which provides somewhat better mortality. However, none of these methods of gene transfer is suitable to treat large numbers of fertilized shrimp eggs at one time, and most importantly, none of these methods raise the potential transformed shrimp into the mature stage.

Transgenic techniques provide a potential tool in producing shrimp capable of combating diseases and, subsequently, improving aquaculture production. However, at present, transgenic shrimp studies suffer from the lack of availability of suitably efficient methods for the introduction of foreign DNA into the very fragile shrimp zygotes. What is needed is a method of in vivo DNA delivery into the eggs of shrimp and other that provides improved ease of use, improved efficiency of transformation, and improved mortality rates over the existing methods.

The present invention is directed to overcoming these and other deficiencies in the art.

SUMMARY OF THE INVENTION

The present invention relates to a method of nucleic acid molecule delivery into a fertilized egg. This method involves providing a fertilized egg prior to its formation of a protective layer, providing a nucleic acid molecule, and combining the nucleic acid molecule and the fertilized egg under conditions effective to allow the nucleic acid molecule to be delivered into the egg.

The present invention provides a simple, inexpensive, non-viral method of nucleic acid molecule delivery into a fertilized egg that results in high gene transfer efficiency with minimal physical damage to the egg.

BRIEF DESCRIPTION OF THE DRAWINGS

FIG. 1A shows 5 minutes post-spawning; FIG. 1B shows 9 minutes post-spawning; FIG. 1C shows 13 minutes post-spawning belly layer formation can be seen), and FIG. 1D shows 55 minutes post-spawning.

FIG. 6 is an ethidium bromide/agarose gel photo showing the results of transfection of DNA with and without transfecting reagents. Lane 1: Effectene™ plus plasmid DNA. Lane 2: Plasmid DNA alone, no transfection reagent. Lane 3: Negative control (no DNA). Lane 4: Effectene™ alone, no DNA. Lane 5: Positive control. Lane 6: Molecular Weight Marker. All samples represent eggs treated at 7–12 minutes post-spawning.

FIG. 7 is an ethidium bromide/agarose gel photo showing the results of transfection of shrimp eggs in various times post-spawning ("p-sp"). Lane 1: Control. Lanes 2, 3, and 4, Superfect reagent plus plasmid DNA at 4–10 minutes, 11–16 minutes, and 17–22 minutes post-spawning, respectively. Lanes 5 and 6, Lipofectamine 2000 reagent with plasmid DNA, at 4–16 and 17–22 minutes post-spawning, respectively. Lanes 7, 8, 9, and 10: plasmid DNA alone, no transfection reagent, at 4–10 minutes, 11–16 minutes, 17–22 minutes, and 24 minutes post-spawning, respectively. Lane 11: Molecular Weight Marker (MWM). Lane 12: TSV-CP (AS) only.

DETAILED DESCRIPTION OF THE INVENTION

Figure 1:
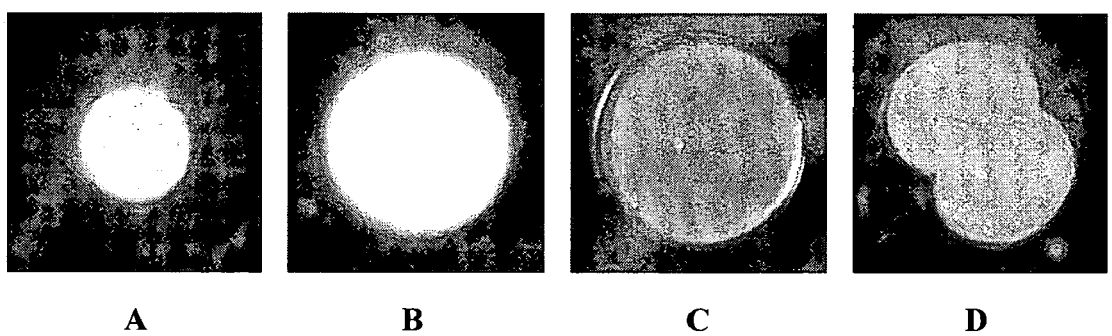
FIGS. 1A–D are photos of embryonic development of *Litopenaeus vannamei* zygotes.

The present invention relates to a method of nucleic acid molecule delivery into a fertilized egg. This method involves providing a fertilized egg prior to its formation of a protective layer, providing a nucleic acid molecule, and combining the nucleic acid molecule and the fertilized egg under conditions effective to allow the nucleic acid molecule to be delivered into the egg. Reproduction in aquatic species often involves the female spawning their eggs directly into the environment, either just prior to or following fertilization. Eggs spawned into the water generally undergo the development of a protective layer following fertilization. Prior to the formation of the protective layer, often referred to as the "jelly coat," the egg is soft and vulnerable to being permeated. It is in this developmental stage that the sperm is able to penetrate and fertilize the egg. In the present invention, this "window of opportunity" is utilized to insert a nucleic acid molecule of interest into the egg, thereby maximizing transfection efficiency and minimizing mechanical harm to the egg. In the present invention, the delivery of a nucleic acid molecule of interest to an egg is carried out prior to the full formation of the protective coating that forms on the egg following the fertilization event.

Combining a nucleic acid molecule of interest with an egg involves conventional recombinant DNA technology. Generally, this involves first inserting a nucleic acid molecule of interest into an expression vector to which the nucleic acid molecule is heterologous (i.e., not normally present). Alternatively, the nucleic acid molecule may be homologous to the species being transformed. A vector is generally constructed to include a promoter, and, if desired, other 5' regulatory elements, a nucleic acid molecule targeted for transcription and/or expression, and a 3' regulatory region having suitable transcriptional termination signals.

"Vector" is used herein to mean any genetic element, such as a plasmid, phage, transposon, cosmid, chromosome, which is capable of replication when associated with the proper control elements, and which is capable of transferring gene sequences between cells. Thus, the term includes cloning and expression vectors, as well as viral vectors, including adenoviral and retroviral vectors. Vectors suitable in the present invention include circularized vectors and linear vectors.

In one aspect of the present invention, the vector is a covalently closed, double-stranded, linear DNA molecule. Such vectors contain only an expression cassette (promoter, coding sequence, and terminator/poly-A-site) of the gene of interest. Linear DNA vectors can be used as minimalistic transfection vectors. Such vectors can be made using methods known in the art, such as described in Sambrook et al., *Molecular Cloning: A Laboratory Manual*, Third Edition, Cold Spring Harbor: Cold Spring Harbor Laboratory Press, New York (1989); Ausubel et al., "Current Protocols in Molecular Biology," Wiley & Sons, Inc., (1993); Watson et al., Recombinant DNA, Scientific American Books, pp. 63–127 (1992), which are hereby incorporated by reference in their entirety, or purchased from a scientific supply company (e.g., MIDGE® ("Minimalistic Immunologically Defined Vectors for Gene Expression," Fermentas, Inc., Hanover, Md.; Nature Technology Corporation, Lincoln, Nebr.). MIDGE® minimalistic transfection vectors, for example, combine the advantages of viral vectors (cell specificity and high expression levels) with those of plasmid vectors (no immunogenicity or danger of viral recombination and relatively low costs).

In another aspect of the present invention, the vector is a circular vector, for example, a circularized plasmid vector.

Exemplary vectors include, without limitation, the following: lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et al., "Use of T7 RNA Polymerase to Direct Expression of Cloned Genes," *Gene Expression Technology* Vol. 185 (1990), which is hereby incorporated by reference in its entirety), and any derivatives thereof. Recombinant genes may also be introduced into viruses, such as vaccinia virus. Recombinant viruses can be generated by transfection of plasmids into cells infected with virus. Plasmid vectors are preferable to viral vectors when used for eggs that may be utilized as a human food source.

Construction of an effective expression vector is an important step toward implementing the genetic transformation process in animals. The expression vector is generally composed of three elements: a promoter, a target gene, and a region having transcriptional termination signals. Among these three components, a suitable promoter is the most important element for a successful gene transformation system. The promoter determines where, when, and under what conditions the nucleic acid of interest should be turned on (i.e., expressed).

A suitable promoter that is appropriate for aquaculture and acceptable to consumers should ideally be derived from marine origin and should not pose any potential health hazards. Several fish gene promoters have been successfully isolated and used to drive foreign gene expression (Jankowski et al., "The GC Box as a Silencer," *Biosci. Rep.* 7:955–63 (1987); Zafarullah et al., "Structure of the Rainbow Trout Metallothionein B Gene and Characterization of its Metal-Responsive Region," *Mol. Cell. Biol.* 8:4469–76 (1988); Liu et al., "Development of Expression Vectors for Transgenic Fish," *Bio/Technology* 8:1268–1272 (1990b); Gong et al., "Functional Analysis and Temporal Expression of Promoter Regions From Fish Antifreeze Protein Genes in Transgenic Japanese Medaka Embryos," *Mol. Mar. Biol. Biotechnol.* 1(1):64–72 (1991); Du et al., "Growth Enhancement in Transgenic Atlantic Salmon by the Use of Fish Antifreeze/Growth Hormone Chimeric Gene Constructs," *Biotechnology* 10:176–81 (1992); Gong et al., "Transgenic Fish in Aquaculture and Developmental Biology," *Current Topic in Develop. Biol.* 30:175–213 (1995); Chen et al., "Transgenic Fish and Aquaculture," *Biotechnol. Apl.* 13(1): 50 (1996); Chan et al., "PCR Cloning and Expression of the Molt-Inhibiting Hormone Gene for the Crab (*Charybdis feriatus*)," Gene 224:23–33 (1998); Gong, "Zebrafish Expressed Sequence Tags and Their Applications," *Meth. Cell Biol.* (zebrafish volume) 60:213–233 (1998); Ju et al., "Faithful Expression of Green Fluorescent Protein (GFP) in Transgenic Zebrafish Embryos Under Control of Zebrafish Gene Promoters," *Dev. Genet.* 25(2):158–67 (1999); Yoshizaki et al., "Germ Cell-Specific Expression of Green Fluorescent Protein in Transgenic Rainbow Trout Under Control of the Rainbow Trout Vasa-Like Gene Promoter," *Int. J. Dev. Biol.* 44(3):323–6 (2000), which are hereby incorporated by reference in their entirety). Other promoters used in transgenic marine fish include mouse metallothionein (McEvoy et al., "The Expression of a Foreign Gene in Salmon Embryos," *Aquaculture* 68:27–37 (1988); Rahman et al., "Fish Transgene Expression by Direct Injection Into Fish Muscle," *Mol. Mar. Biol. Biotechnol.* 1:286–289 (1992), which are hereby incorporated by reference in their entirety), heat shock promoters (Bayer et al., "A Transgene Containing lacZ is Expressed in Primary Sensory Neurons in Zebrafish," *Development* 115:421–446 (1992); Krone, "Several Unique Hsp 90 Genes are Expressed During Embryonic Development of Zebrafish," Presented at Symposium on Advances in Molecular Endocrinology of Fish, May 23–25, Toronto, Canada (1993), which are hereby incorporated by reference in their entirety), chicken β-actin promoter (Lu et al., "Integration and Germline Transmission of Human Growth Hormone Gene in Medaka (*Oryzias latipes*)," presented at Second International Marine Biotechnology Conference, 1991, Baltimore, Md. (1991); Inoue et al., "Introduction, Expression, and Growth-Enhancing Effect of Rainbow Trout Growth Hormone cDNA Fused to an Avian Chimeric Promoter in Rainbow Fry," *J. Mar. Biotechnol.* 1: 131–4 (1993) which are hereby incorporated by reference in their entirety), carp β-actin promoter (Liu et al., "Functional Analysis of Elements Affecting Expression of the β-Actin Gene of Carp," *Mol. Cell Biol.* 10:3432–3440 (1990); Rahman et al., "Fish Transgene Expression by Direct Injection Into Fish Muscle," *Mol. Mar. Biol. Biotechnol.* 1:286–289 (1992), which are hereby incorporated by reference in their entirety), the antifreeze protein promoter from the ocean pout (*Macrozoarces americanus*) (Gong et al., "Functional Analysis and Temporal Expression of Promoter Regions From Fish Antifreeze Protein Genes in Transgenic Japanese Medaka Embryos," *Mol. Mar. Biol. Biotechnol.* 1(1):64–72 (1991); Hew et al., "Antifreeze Protein Gene Transfer in Atlantic Salmon," Presented at Second International Marine Biotechnology Conference, 1991, Baltimore, Md. (1991); Du et al., "Growth Enhancement in Transgenic Atlantic Salmon by the Use of Fish Antifreeze/Growth Hormone Chimeric Gene Constructs," *Biotechnology* 10:176–81 (1992), which are hereby incorporated by reference in their entirety), and the histone promoter from the trout (Muller et al., "Introducing Foreign Genes Into Fish Eggs With Electroporated Sperm as a Carrier," *Mol. Mar. Biol. Biotechnol.* 1:276–281 (1992), which are hereby incorporated by reference in their entirety).

Examples of promoters useful in the present invention include, without limitation, the actin or β-actin nucleic acid promoter molecule derived from shrimp, chicken, or other sources. The β-actin and actin promoters are constitutive, non-inducible, non-developmental promoters. A constitutive promoter is a promoter that directs expression of a gene throughout the development and life of an organism. β-actin and actin promoters are suitable in the present invention, linked in the nucleic acid construct of the present invention to one or more nucleic acid molecules encoding a target protein or polypeptide of interest for which constitutive expression in the selected host is desired. Alternatively, an inducible or repressible promoter may be included in the vector when external, developmental, or site-specific control of expression is desired.

Any nucleic acid molecule(s) of interest may be operably linked to a suitable promoter molecule in a suitable vector for transformation and/or transfection using the method described herein, including but not limited to, nucleic acids encoding viral proteins, such as coat proteins; growth regulating proteins; and proteins relating to enhanced stress tolerance in hosts transformed with such nucleic acid molecules, including heat shock proteins for increasing tolerance to cold-related stress.

Also present in the vector is a 3' regulatory region containing suitable transcription termination signals selected from among those which are capable of providing correct transcription termination and polyadenylation of mRNA for expression in the host cell of choice, operably linked to a nucleic acid molecule which encodes for a protein or polypeptide of choice. An example of a commonly-used 3' regulatory element for expression of genes of interest in animal cells is the SV40 polyadenylation signal derived from the SV40 virus. Virtually any 3' regulatory element known to be operable in the host cell of choice will suffice for proper expression of the nucleic acid molecules using the transformation method of the present invention.

Also suitable in the nucleic acid construct of the present invention is a reporter gene (marker gene). Exemplary markers genes include, without limitation, β-galactosidase, luciferase, green fluorescent protein (GFP) or enhanced green fluorescent protein (EGFP) gene of the bioluminescent jelly fish, *Aequorea victoria* (Inoue, "Expression of Reporter Genes Introduced by Microinjection and Electroporation in Fish Embryos and Fry," *Mol. Mar. Biol. and Biotechnol.* 1(4/5): 266–270 (1992); Boulo et al., "Transient Expression of Luciferase Reporter Gene After Lipofection in Oyster (*Crassostrea gigas*) Primary Cell Cultures," *Mol. Mar. Biol. Biotechnol.* 5(3): 167–74 (1996); Guillen et al., "Reporter Genes for Transgenic Fish Experiments," *Biotechnol. Apl.* 13(4):279–283 (1996); Arnone et al., "Green Fluorescent Protein in the Sea Urchin: New Experimental Approaches to Transcriptional Regulatory Analysis in Embryos and Larvae," *Development* 124(22):4649–4659 (1997); Husebye et al., "A Functional Study of the Salmon GnRH Promoter," *Mol. Mar. Biol. Biotechnol.* 6(4):357–363 (1997); Joore et al., "Regulation of the Zebrafish Goosecoid Promoter by Mesoderm Inducing Factors and Xwnt1," *Mech. Dev.* 55:3–18 (1997), which are hereby incorporated by reference in their entirety).

The expression of the reporter gene serves as a marker to identify those recipients in which gene delivery has been successful, and helps to distinguishing the organs and tissues in which the promoter is capable of driving target nucleic acid expression (Watson et al., "New Tools for Studying Gene Function," In: *Recombinant DNA*, New York: Scientific American Books, pp. 191–272 (1992); Winkler et al., "Analysis of Heterologous and Homologous Promoters and Enhancers in vitro and in vivo by Gene Transfer Into Japanese Medaka (*Oryzias latipes*) and Xiphophorus," *Mol. Mar. Biol. and Biotechnol.* 1 (4/5):326–337 (1992), which are hereby incorporated by reference in their entirety).

In one aspect of the present invention, the nucleic acid molecule itself is labeled to allow for tracking the movement of the nucleic acid molecule after delivery of the nucleic acid to the egg. Thus, the movement of the nucleic acid molecule can be determined even without gene expression. This involves labeling a selected nucleotide of the nucleic acid molecule directly with a label. Alternatively, nucleotides of the vector are directly labeled to allow for tracking the movement of the nucleic acid molecule after delivery to the egg without the need for gene expression. Suitable labels for these aspects of the present invention include, without limitation, radioactive labels, fluorescent labels, chemiluminescent labels, and biotinylated labels. Methods of labeling the nucleic acid molecule can be used that are well-known in the art, and detection of the label will be understood by one of skill in the art to be dependent upon the label selected.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The nucleic acid expression vector, which contains a promoter, may also contain any combination of various "strong" transcription and/or translation initiation signals. For instance, efficient translation in *E. coli* requires a Shine-Dalgarno ("SD") sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used. For a review on maximizing gene expression see Roberts and Lauer, *Methods in Enzymology,* 68:473 (1979), which is hereby incorporated by reference in its entirety.

Depending on the vector system and host utilized, any number of suitable transcription and/or translation elements, including constitutive, inducible, and repressible promoters, as well as minimal 5' promoter elements may be used.

A suitable promoter molecule, a nucleic acid molecule encoding a protein or polypeptide of interest, a suitable 3' regulatory region, and if desired, a reporter or marker gene, are incorporated into a vector-expression system of choice to prepare the nucleic acid construct of present invention using standard cloning procedures known in the art, such as described by Sambrook et al., *Molecular Cloning: A Laboratory Manual*, Third Edition, Cold Spring Harbor: Cold Spring Harbor Laboratory Press, New York (1989); Ausubel et al., "*Current Protocols in Molecular Biology,*" Wiley &

Sons, Inc., (1993); Watson et al., *Recombinant DNA*, Scientific American Books, pp. 63–127 (1992), which are hereby incorporated by reference in their entirety, and U.S. Pat. No. 4,237,224 to Cohen and Boyer, which is hereby incorporated by reference in its entirety, which describes the production of expression systems in the form of recombinant plasmids using restriction enzyme cleavage and ligation with DNA ligase. A nucleic acid molecule encoding a protein of choice may be inserted into a vector in the sense (i.e., 5'→3') direction, such that the open reading frame is properly oriented for the expression of the encoded protein under the control of a promoter of choice. Single or multiple nucleic acids may be ligated into an appropriate vector in this way.

Alternatively, one or more nucleic acids encoding a protein of choice is inserted into the vector in an antisense orientation (3'→5'). The use of antisense RNA to downregulate the expression of specific genes is well known (van der Krol et al., "Antisense Genes in Plants: An Overview," *Gene* 72:45–50 (1988); van der Krol et al., "Inhibition of Flower Pigmentation by Antisense CHS Genes: Promoter and Minimal Sequence Requirements for the Antisense Effect," *Plant Mol Biol* 14(4):457–66 (1990); Mol et al., "Regulation of Plant Gene Expression by Antisense RNA," *FEBS Lett* 286:427–430 (1990); and Smith et al., *Nature*, 334:724–726 (1988); which are hereby incorporated by reference in their entirety). Antisense nucleic acids are DNA or RNA molecules that are complementary to at least a portion of a specific mRNA molecule (Weintraub, "Antisense RNA and DNA," *Scientific American* 262:40 (1990), which is hereby incorporated by reference in its entirety). Antisense methodology takes advantage of the fact that nucleic acids tend to pair with "complementary" sequences. By complementary, it is meant that polynucleotides are capable of base-pairing according to the standard Watson-Crick rules. In the target cell, the antisense nucleic acids hybridize to a target nucleic acid and interfere with transcription, and/or RNA processing, transport, translation, and/or stability. The overall effect of such interference with the target nucleic acid function is the disruption of protein expression.

Accordingly, both antisense and sense forms of the nucleic acids of the present invention are suitable for nucleic acid constructs used to practice the invention. A single construct may contain both sense and antisense forms of one or more desired nucleic acids encoding a protein.

Alternatively, the nucleic acid construct of the present invention may be configured so that the DNA molecule encodes an mRNA which is not translatable, i.e., does not result in the production of a protein or polypeptide. This is achieved, for example, by introducing into the desired nucleic acid sequence of the present invention one or more premature stop codons, adding one or more bases (except multiples of 3 bases) to displace the reading frame, and removing the translation initiation codon (U.S. Pat. No. 5,583,021 to Dougherty et al., which is hereby incorporated by reference in its entirety). This can involve the use of a primer to which a stop codon, such as TAA or TGA, is inserted into the sense (or "forward") PCR-primer for amplification of the full nucleic acid, between the 5' end of that primer, which corresponds to the appropriate restriction enzyme site of the vector into which the nucleic acid is to be inserted, and the 3' end of the primer, which corresponds to the 5' sequence of the enzyme-encoding nucleic acid.

Genes can be effective as silencers in the non-translatable antisense forms, as well as in the non-translatable sense form (Baulcombe, D.C., "Mechanisms of Pathogen-Derived Resistance to Viruses in Transgenic Plants," *Plant Cell* 8:1833–44 (1996); Dougherty et al., "Transgenes and Gene Suppression: Telling us Something New?" *Current Opinion in Cell Biology* 7:399–05 (1995); Lomonossoff, G. P., "Pathogen-Derived Resistance to Plant Viruses," *Ann. Rev. Phytopathol.* 33:323–43 (1995), which are hereby incorporated by reference in their entirety). Accordingly, the present invention is meant to include nucleic acid vectors which contain one or more of the nucleic acid molecules of the present invention as a nucleic acid which encodes a non-translatable mRNA, that nucleic acid molecule being inserted into the vectors in either the sense or antisense orientation.

Once the isolated nucleic acid molecule of choice has been cloned into an expression system, it is ready to be incorporated into a host cell. Recombinant molecules can be introduced into cells via transformation, particularly transduction, conjugation, lipofection, protoplast fusion, mobilization, particle bombardment, or electroporation. The nucleic acid sequence(s) are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Transient expression in protoplasts allows quantitative studies of gene expression since the population of cells is very high (on the order of $10^6$). To deliver DNA inside protoplasts, several methodologies have been proposed, but the most common are electroporation (Neumann et al., "Gene Transfer into Mouse Lyoma Cells by Electroporation in High Electric Fields," *EMBO J.* 1: 841–45 (1982); Wong et al., "Electric Field Mediated Gene Transfer," *Biochem Biophys Res Commun* 30; 107(2):584–7 (1982); Potter et al., "Enhancer-Dependent Expression of Human Kappa Immunoglobulin Genes Introduced into Mouse pre-B Lymphocytes by Electroporation," *Proc. Natl. Acad. Sci. USA* 81: 7161–65 (1984), which are hereby incorporated by reference in their entirety) and polyethylene glycol (PEG) mediated DNA uptake, Sambrook et al., *Molecular Cloning: A Laboratory Manual*, Chap. 16, Second Edition, Cold Springs Laboratory, Cold Springs Harbor, N.Y. (1989), which is hereby incorporated by reference in its entirety). During electroporation, the nucleic acid molecule is introduced into the cell by means of a reversible change in the permeability of the cell membrane due to exposure to an electric field. PEG transformation introduces the nucleic acid by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, including minicells, cells, lysosomes, or other fusible lipid-surfaced bodies that contain the chimeric gene. Fraley, et al., *Proc. Natl. Acad. Sci. USA,* 79:1859–63 (1982), which is hereby incorporated by reference in its entirety.

Stable transformants are preferable for the methods of the present invention, which can be achieved by using variations of the methods above as describe in Sambrook et al., *Molecular Cloning: A Laboratory Manual*, Chap. 16, Second Edition, Cold Springs Laboratory, Cold Springs Harbor, N.Y. (1989), which is hereby incorporated by reference in its entirety.

Once the expression vector containing the nucleic acid molecule of choice is delivered into a suitable host cell, the host organism is grown under conditions suitable to amplify the host. The vector/nucleic acid construct is then isolated from the amplified host population according to methods well known in the art. An exemplary system would include an E. coli host transformed with the desired DNA/vector construct and amplified in a suitable liquid medium containing the appropriate antibiotic (Sambrook et al., *Molecular Cloning: A Laboratory Manual*, Chap. 16, Second Edition, Cold Springs Laboratory, Cold Springs Harbor, N.Y. (1989), which is hereby incorporated by reference in its entirety). Transformants can be easily identified by the selectable marker encoded by the plasmid e.g., antibiotic resistance in bacterial host cells and the resulting phenotype of those bacterial cells. The transformed host bacteria are recovered by centrifugation and lysed by any one of a large number of methods, including treatment with nonionic or ionic detergents, organic solvents, alkali, or heat, and the plasmid DNA is isolated, further purified if desired, and quantified using methods such as those described in Sambrook et al., *Molecular Cloning: A Laboratory Manual*, Chap. 16, Second Edition, Cold Springs Laboratory, Cold Springs Harbor, N.Y. (1989), which is hereby incorporated by reference in its entirety. Any of the multitude of commercially available systems is also suitable for plasmid DNA isolation.

In one aspect of the present invention the nucleic acid molecule of choice is not associated with a vector. In this aspect, the nucleic acid molecule is operably linked to a desired promoter and terminator/poly-A-site sequences, but is not contained in an expression cassette. When the desired nucleic acid molecule is a DNA molecule, the nucleic acid is referred to as "naked DNA." Development of naked DNA transfection is attractive. It provides advantages over vector-based transfection methods, e.g. simplicity of construction, ease of large scale production, cost-effectiveness, lower toxicity and immunogenicity, and eliminates the introduction of exogenous genes associated with vectors, especially viral vector systems (Chen et al., "Enhancement of Naked FIX Minigene Expression of Chloroquine in Mice," *Acta Pharmacologica Sinica* 25(5):570–575 (2004), which is hereby incorporated by reference in its entirety).

Once the plasmid DNA is isolated, it is ready to be incorporated into an egg of the chosen organism. Suitable methods of combining the recombinant nucleic acid molecule and the egg include physical methods (e.g., microinjection, electroporation), chemical methods (transfection reagents), or a combination thereof.

As discussed herein above, the most commonly used methods of transferring foreign nucleic acid into marine and fresh water species are electroporation, ballistic bombardment, and microinjection. In one aspect of the present invention, microinjection is used to carry out the delivery of the nucleic acid molecule into the fertilized egg. Microinjection can be carried out as described in the art (Chong et al., "Expression and Fate of CAT Reporter Gene Microinjected into Fertilized Medaka (*Oryzias latipes*) Eggs in the Form of Plasmid DNA, Recombinant Phage Particles and its DNA," *Theor. Appl. Genet.* 78:369–380 (1989), Penman et al., "Factors Effecting Survival and Integration Following Micro-Injection of Novel DNA in Rainbow Trout Eggs," *Aquaculture* 85:35–50 (1990); Collas et al., "Transferring Foreign Genes into Zebrafish Eggs By Microinjection," In Houdebine, L. M. (ed.) *Transgenic Animals—Generation and Use*, Harwood Academic Publishers (In Press); which are hereby incorporated by reference in their entirety) or as described in greater detail herein in Example 4, below. The nucleic acid molecule of choice may be injected into the host egg using only a physiologically suitable carrier, for example, sterile saline, or the nucleic acid construct may be combined with a transfecting agent for microinjection, including, but not limited to, those described herein below.

In another aspect of the present invention, transfer of the nucleic acid molecule of interest is carried out using a transfection reagent. Transfection reagents are useful as a nucleic acid carrier in the present invention because they are non-toxic and self-degrading, and, thus, have no residual affect on the growth and development of the recipient organism. There are a variety of transfection reagents suitable for use in the present invention that are known in the art. These include, without limitation, calcium phosphate (Sambrook et al., *Molecular Cloning: A Laboratory Manual*, Chap. 16, 16:30–16.40, Second Edition, Cold Springs Laboratory, Cold Springs Harbor, N.Y. (1989), which is hereby incorporated by reference in its entirety), "Calcium Phosphate Transfection System," Invitrogen, Carlsbad, Calif.; "CellPhect™ Transfection Kit," Amersham Biosciences, Piscataway, N.J.); DEAE-dextran (Sambrook et al., *Molecular Cloning: A Laboratory Manual*, Chap. 16, 16:41–16.46, Second Edition, Cold Springs Laboratory, Cold Springs Harbor, N.Y. (1989), which is hereby incorporated by reference in its entirety); cationic lipid reagents (e.g., TransFectin™ Lipid Reagent, Bio-Rad, Hercules, Calif.); activated dendrimers (e.g., Superfect™ and Polyfect, Qiagen, Valencia, Calif.); liposomal cationic lipid reagents (e.g., Lipofectamine 2000, Invitrogen, Carlsbad, Calif.), cationic non-liposomal lipid reagents (e.g., Effectene™, Qiagen, Valencia, Calif.), and cationic polymer polyethyleneimine (PEI) reagents (e.g., ExGen, Fermentas, Inc., Hanover, Md.; Polyethyleneimine-Transferrinection, Bender MedSystems, San Bruno, Calif., jetPEI™, Qbiogene, Carlsbad, Calif.). In one aspect of the present invention, the vector containing a nucleic acid molecule of interest is combined with a polyethyleneimine transfection reagent for delivery into an egg. In another aspect of the present invention, the transfection reagent is a linear polyethyleneimine transfection reagent (e.g., jetPEI™, Qbiogene, Carlsbad, Calif.).

Animals suitable for all aspects of the present invention include, without limitation, marine fish, freshwater fish, crustaceans, including prawns and shrimp, shellfish, and insects.

In all aspect of the present invention, the delivery of the desired DNA is timed so as to occur prior to the finalization of the jelly layer, or the protective covering of any egg that is the equivalent of the shrimp "jelly layer." One skilled in the art will recognize that the optimal time post-spawning may vary from that of the white shrimp egg, described herein. The developmental stages of a protective layer have been determined for many fish and crustaceans. For any chosen species the optimal time post-spawning is easily determined by the investigator using methods well-known in the art, or as described herein below.

EXAMPLES

Example 1

Timing after Spawning

Mature fertilized shrimp eggs contain large cortical specializations (rods) in their cortex. These rods reside in membrane crypts and are isolated from the external environment by a thin investment coat which surrounds the egg.

When the eggs contact seawater in the form of spawning, their cortical rods are expelled and form an investment coat, which subsequently dissipates. At this stage, the egg is naked without any coating material. About 12–18 minutes after spawning, a new jelly layer begins to form around the egg's exterior. This jelly layer appears to be very sturdy and sticky and serves as a protective layer during the embryonic development of the shrimp egg.

Over a timed course of approximately 50 minutes (one-cell stage), pictures were continuously taken to observe the embryonic development of the shrimp *Litopenaeus vannamei*. Five minutes, nine minutes, thirteen minutes, and fifty-five minutes post-spawning results are shown in FIGS. 1A, 1B, 1C, and 1D, respectively. In approximately 20–45 minutes after spawning, the jelly layer is fully formed into a hatching membrane.

Example 2

Animals

Mature gravid female shrimp, *Litopenaeus vannamei*, (specific pathogen free, SPF) were obtained from a local shrimp farm (Chen-Lu Farms, Inc., Kahuku, Hi.). Immediately after spawning, the shrimp eggs were collected, concentrated, and transferred to 3 ml sterilized sea water in a petri dish and subjected to microinjection, electroporation, and transfection with jetPEI™ (Qbiogene, Carlsbad, Calif.) as described in greater detail below.

Example 3

Expression Vector Construction

Figure 2:
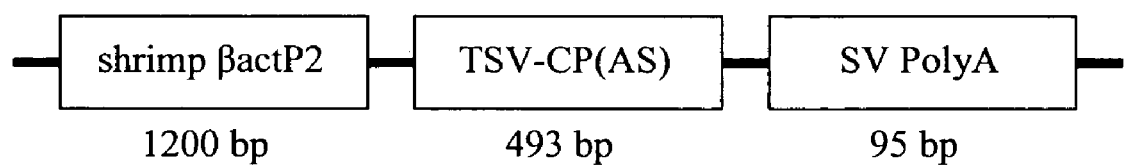
FIG. 2 is a map of the expression vector, pβactP2-TSV-CP(AS) used for shrimp egg transformation.

Expression vector construction was carried out as described in Sun, P.S., "Recombinant Molt-Inhibiting Hormone-Like Neuropeptide Produced in the Yeast *Pichia pastoris*," In: *PACON International Proceedings*, Aug. 6–8, 1997, Hong Kong, China, pp. 509–518 (1997), which is hereby incorporated by reference in its entirety. Briefly, the expression vector consisted of the chimeric shrimp β-actin promoter from *L. vannamei* and a 493 bp partial sequence of the target gene, a coat-protein-encoding gene of the Taura Syndrome Virus ("TSV-CP") (Mari et al., "Full Nucleotide Sequence and Genome Organization of the Taura Syndrome Virus of Penaeid Shrimp," Unpublished (2000); Genbank Accession Number: AF277675, which are hereby incorporated by reference in their entirety). The vector was constructed as described in WO 03/04825, which is hereby incorporated by reference in its entirety. The pSV-β-galactosidase vector (Promega, Madison, Wis.) was used as the base vector. Using standard PCR techniques, Nco I and Hind III restriction enzyme sites were created at the 5' end and 3' end, respectively, of the β-actin shrimp promoter, βactP2. The SV40 promoter and enhancer of the pSV-β-galactosidase vector were excised through restriction enzyme digestion with Nco I and Hind III, and the βactP2 was inserted into the vector to construct the expression vector, pβactP2-β-Gal. In addition, Hind III and Sal I restriction enzyme sites were added to the 493-bp TSV-CP target gene. Again using standard PCR, the lacZ gene of the pβactP2-β-Gal vector was replaced with the TSV-CP(AS) target gene in antisense orientation, thus producing the expression vector, pβactP2-TSV-CP(AS). General procedures of ligation, cloning, and plasmid DNA purification followed the methods of Sambrook et al., *Molecular Cloning: A Laboratory Manual*, $2^{nd}$ ed. Cold Spring Harbor, N.Y.: Cold Spring Harbor Laboratory Press (1989), which is hereby incorporated by reference in its entirety. A map of the expression vector, pβactP2-TSV-CP(AS), is shown in FIG. 2.

It is necessary to clarify why the expression vector pβactP2-TSV-CP(AS) was used in this method instead of using commercially available expression vectors. At the beginning of this work, a suitable reporter gene for monitoring gene expression in shrimp was researched. Since the presence of endogenous fluorescent compounds in shrimp had been reported (Latz et al., "Slow Photic and Chemical Induction of Bioluminescence in the Midwater Shrimp, *Sergestes similis* Hansen," *Biol. Bull.* 182:391–400 (1992), which is hereby incorporated by reference in its entirety), the endogenous fluorescent compounds in various organs and developmental stages of the marine shrimp, *L. vannamei*, were examined using fluorescence microscopy and spectrofluorometric analysis. It was observed that most of the shrimp organs exhibited major fluorescent intensity at excitation wavelengths between 250 nm and 530 nm (Arakaki et al., "Endogenous Fluorescence in Shrimp During Development and in Adult Organs," In: *Postgraduate Conference on Marine Biology and Biotechnology*, Jun. 6–8, 2001, Hong Kong, China, p. 70. (2001), which is hereby incorporated by reference in its entirety). Since reporter protein EGFP exhibits its emission maxima at 507 nm (Clontech, Palo Alto, Calif.), it is expected that interference in fluorescence may occur between the shrimp endogenous fluorescent compounds and the reporter protein, EGFP.

When transfection experiments were carried out on shrimp zygotes with vector pCMV-EGFP-N1 with the transfecting reagent jetPEI™, it was found that at the postlarval stage 20, very low fluorescent intensity was generated in the experimental shrimp. In contrast, the control shrimp exhibited an unexpectedly high fluorescent intensity, which was believed to be derived from the endogenous fluorescent compounds of the shrimp. However, during several development stages (nauplii, mysis, and postlarvae) of the experimental shrimp, the reporter gene EGFP was detected via RT-PCR assay, suggesting that EGFP was present at the gene transcriptional level. It is unclear whether the half-life of the protein EGFP is very short or extremely labile in the shrimp system. Therefore, based on these findings, an in-house expression vector, pβactP2-TSV-CP(AS), was constructed for use where the TSV-CP(AS) served as the target gene and was driven by the shrimp beta-actin promoter P2. Other expression vectors suitable in the present invention include those known in the art or later discovered that are suitable for use with the desired organism from which the eggs to be transfected are derived.

Example 4

Microinjection

Immediately after spawning, the shrimp eggs were concentrated by filtering through a coffee filter unit and transferred to sterilized sea water containing 1 mM 3-amino-1, 2,4-triazole (ATA) to facilitate micropipette penetration of the hatching envelope. The eggs were transferred into a petri dish coated with a thick layer of agarose gel as a soft support. A 220 μm fine nylon mesh was placed on top of the gel to prevent the eggs (penaeid shrimp eggs have a diameter of approximately 250 μm) from rolling during injection. During injection, the eggs were immersed in sterile seawater and viewed through a high-power stereo dissecting microscope (Carl Zeiss, Jena, Germany). Microinjection was performed between 10 to 50 minutes after egg fertilization, at the one-cell stage, shown in FIGS. 1A–D, with the Eppendorf Femtojet microinjection system (Fisher Scientific, St. Louis, Mo.). Each egg was injected with 20–40 pl (equivalent to ~0.5% of the total egg volume) of the plasmid DNA at μg/μl of pβactP2-TSV-CP (AS) in distilled water. After injection, eggs were placed in a 1 liter beaker with aerated seawater (28° C.) containing 0.15 ppm each of penicillin and streptomycin. Gene expression was monitored via RT-PCR or genomic PCR assay, as described in Example 8, below. Several microinjection experiments were performed and the hatching rate, gene expression efficiency, and survival rate of each experiment were recorded. Control shrimp eggs were microinjected with 20–40 pl of distilled water without the plasmid DNA.

Microinjection is generally considered to be the most tedious, but also the most precise, method for transferring a nucleic acid molecule of interest into the host organism. It allows precision in the delivery of exogenous DNA and often results in high efficiency of gene transformation (Chong et al., "Expression and Fate of CAT Reporter Gene Microinjected into Fertilized Medaka (*Oryzias latipes*) Eggs in the Form of Plasmid DNA, Recombinant Phage Particles and its DNA," *Thor. Appl. Genet.* 78:369–380 (1989); Maclean et al., "Transgene Transmission and Expression in Rainbow Trout and Tilapia," *Mol. Mar. Biol. Biotechnol.* 1:355–365 (1992); Cadoret et al., "Microinjection of Bivalve Eggs: Application in Genetics," *Mol. Mar. Biol. Biotechnol.* 6:72–77 (1997), which are hereby incorporated by reference in their entirety). Delivery of the expression vector, pβactP2-TSV-CP(AS), into shrimp zygotes via microinjection is complicated by the extremely low hatching rate and shortened life span of microinjected shrimp as a result of intensive injection-related physiological trauma. Table 1, below, summarizes various parameters including post-hatching survival rate, target gene expression, complexity of the methods, and possible number of eggs treated per female shrimp, as well as the hatching rates and efficiency of gene transfer among the three methods tested in this study. When using microinjection, the hatching rate of *L. vannamei* is only 3–5%, which is very low in comparison to the hatching rate of commercially farmed shrimp, which is about 50–60% (Chen-Lu Farms, Kahuku, Hi.). In several trial experiments, although some of the injected eggs hatched and developed normally into the nauplii, mysis, and post-larvae stages, all of the animals died before reaching day 12 of the post-larval stage. The early mortality of the microinjected animals, possibly due to the stress of the surgical procedure, makes it difficult to conduct studies on the stability of the transgene and long-term target gene expression detection. Target gene expression via RT-PCR and genomic PCR was detectable only at the mysis stage, as shown in Table 2, below. Nevertheless, Preston et al., "Delivery of DNA to Early Embryos of the Kuruma Prawn, *Penaeus japonicus*," *Aquaculture* 181:225–234 (2000), which is hereby incorporated by reference in its entirety) examined the relative efficiency of microinjection, electroporation, and particle bombardment for introducing DNA into the embryos of the Kuruma prawn, *Penaeus japonicus*, and found microinjection to be the most reliable technique in terms of gene delivery.

TABLE 1

Summary of DNA delivery into shrimp zygotes using methods of microinjection, electroporation, and transfection reagent

| Method | Hatchability (%) | Post-hatching survival (%) | RT-PCR | Genomic PCR assay | Possible number of eggs treated per female | Complexity of method |
|---|---|---|---|---|---|---|
| Microinjection | 3–5 | 10[a] | +++[b] | Positive[c] | 20–50 | precise but labor intensive |
| Electroporation | 25–35 | 13[a] | +[b] | Positive[c] | 10,000–15,000 | requires optimization of parameters |
| Transfection using jet PEI | 50–60 | 50 | +++++[b] | 64%[d] | 20,000–50,000 | Simple and efficient |

[a] all animals were terminated for target gene detection at mysis stage (one-week-old);
[b] "+" indicates the DNA band intensity from RT-PCR assays performed on groups of five one-week-old shrimp at the mysis stage;
[c] genomic PCR assays were performed on groups of five one-week-old shrimp;
[d] genomic PCR assays were performed using genomic DNA isolated from the swimming legs of individual five-month-old shrimp. Control animals showed negative results in both RT-PCR and genomic PCR assays.

One major advantage that microinjection has over electroporation and transfection methods is that, unlike electroporation and transfection, it is not necessary to undertake the time-consuming task of screening for potentially transgenic shrimp after treatment, since direct injection of the plasmid DNA into the shrimp zygotes seem to be almost certain that the gene is inserted and introduced into the shrimp system. This was evident in most of the microinjection experiments performed as describe herein.

Example 5

Electroporation

Electroporation experiments were carried out with an Electro Square Porator ECM 830 (BTX, San Diego, Calif.) and the Petri Pulser PP35-2P model (BTX, San Diego, Calif.). Optimal conditions for obtaining the highest hatching rate of electroporated shrimp eggs at the one-cell stage, shown in FIGS. 1A–D (i.e., 5–50 minutes post-spawning), were examined by adjusting variable parameters including voltage, electroporation pulse-length, and number of pulses as described by Venzon et al., "Optimization of Electroporation Parameters for Transient Gene Expression in the Pacific White Shrimp, *Litopenaeus vannamei*," In: *World Aquaculture Conference*, May 19–23, 2003, Salvador, Brazil, World Aquaculture Society p. 810 (2003), which is hereby incorporated by reference in its entirety. The settings (field strength of 40 V/cm; pulse length of 10 μs; and 3 pulses) which provided a hatching rate of 35% were used in this study. Circular plasmid DNA was dissolved in 0.77 M mannitol in a total volume of 2 ml at a concentration of 15 μg/ml. Approximately 200 fertilized shrimp eggs were placed in the petri dish (35×10 mm) containing the DNA/mannitol solution. After the electric pulse, the eggs were transferred to a 1-liter beaker containing clean aerated seawater (28° C.). Control shrimp were electroporated without adding DNA into the 0.77 M mannitol and were treated in the same manner as the experimental group. The hatching rate was recorded 24–36 hours after treatment.

Delivery of plasmid DNA into shrimp zygotes via electroporation offers a viable alternative to microinjection as shrimp hatching and survival rates from electroporation are much higher. However, the efficiency of target gene expression via electroporation is much lower than expected, as shown in Table 1. In testing 20 putative transgenic shrimp (85-day-old) after the electroporation process, only three shrimp were detected positive for the target gene, as monitored by RT-PCR indicating a 15% gene transfer efficiency, shown in Table 2, below.

In a separate experiment, genomic DNA was isolated from five putative transgenic shrimp and the transgene was detected positive via PCR, as shown in Table 2, below. In studies on transgenic sea bream, a success rate of 15% for transgenic transformation using the electroporation method was reported, and evidence of gene integration in the sea bream genome by Southern hybridization was shown (Lu, J. K., "Production of Transgenic Marine Organisms by Various Mass Gene Transfer Techniques," In: *Postgraduate Conference on Marine Biology and Biotechnology*, Jun. 6–8, 2001, Hong Kong, China, p. 43 (2001), which is hereby incorporated by reference in its entirety). Electroporation of single-cell embryos in shrimp, *Litopenaeus schimitti*, showed transient β-galactosidase activity in 19.4% of the treated embryos (Arenal et al., "Gene Transfer in Shrimp (*Litopenaeus schimitti*) by Electroporation of Single-Cell Embryos and Injection of Naked DNA into Adult Muscle," *Biotecnologia Aplicada* 17:247–250 (2000), which is hereby incorporated by reference in its entirety). One investigator, electroporating at the two-cell stage of the tiger shrimp (*Penaeus monodon*), found that the survival rate was 0.6% for postlarvae 45 and 0.4% for postlarvae 120, and the gene transfer efficiency was found to be 21% at postlarvae 120 as determined by dot blot analysis (Tseng et al., "Introducing Foreign DNA into Tiger Shrimp (*Penaeus monodon*) by Electroporation," *Theriogenology* 54:1421–1432 (2000), which is hereby incorporated by reference in its entirety). The very low survival rate (0.4%) of the electroporated tiger shrimp clearly indicated that the embryos had sustained extensive damage during electroporation procedures. Despite showing high hatching rates (25 to 35%), the shrimp that had been electroporated at the one-cell stage were unable to survive to postlarvae 20. From these results, it is inferred that shrimp zygotes electroporated at the one-cell stage are not as durable as zygotes electroporated at the two-cell stage. Nevertheless, in order to produce transgenic shrimp (i.e., disease-resistant, growth enhanced) in which introduced target gene expresses in all the organs and tissues of the animals, it is essential to transfer the target gene at the one-cell stage prior to the initial cell division. This eliminates the problem of mosaicism as reported by Tseng et al., "Introducing Foreign DNA into Tiger Shrimp (*Penaeus monodon*) by Electroporation," *Theriogenology* 54:1421–1432 (2000), which is hereby incorporated by reference in its entirety.

TABLE 2

Detection of target gene in experimental shrimp (*Litopenaeus vannamei*).

| | RT-PCR | | | Genomic PCR | | |
|---|---|---|---|---|---|---|
| Method | No. of shrimp tested | No. of positive shrimp | Efficiency (%) | No. of shrimp tested | No. of positive shrimp | Efficiency (%) |
| Microinjection | 5[a] | + | N/A | 5[a] | + | N/A |
| Electroporation | 20[b] | 3 | 15 | 5[a] | + | N/A |
| Transfection using jet PEI | 15[c] | 9 | 60 | 28[c] | 18 | 64 |

[a] due to the small size of the shrimp at the mysis stage (7-day-old shrimp), a group of five animals were used for RNA/DNA isolation;
[b] RT-PCR assay were performed on 85-day-old shrimp;
[c] RT-PCR assay were performed on 150-day-old shrimp.

Example 6

Transfection with jetPEI™

Procedures of preparing vector/sodium chloride and jetPEI™/sodium chloride mixtures followed the vendor's manual (Qbiogene, Carlsbad, Calif.) with slight modification as described by Calderon et al., "Transfection of Shrimp Zygotes Using JetPEI-DNA Complex," In: *Transgenic Animal Research Conference IV*, Aug. 10–14, 2003, Tahoe City, Calif., which is hereby incorporated by reference in its entirety). Briefly, fertilized shrimp eggs approximately five minutes post-spawning were transferred into a petri dish (35×10 mm) containing 1 μg of the expression vector, pβactP2-TSV-CP(AS), containing 1 mg/ml DNA, and 1.2 μl of the transfecting reagent, jetPEI™ (7.8 mM) in 2 ml of sterile seawater. The final reaction mixture of approximately 2.5 ml was incubated at room temperature for 50 minutes prior to transfer into a 1-liter beaker filled with sterile aerated seawater at 28° C. for the hatching process. After recording the hatching rate at 24–36 hours after treatment, the transfected shrimp were transferred to 55-gallon tanks for further maturation. The control shrimp were treated in the same manner except that no plasmid DNA was introduced into the shrimp eggs.

Introducing plasmid DNA into fertilized shrimp eggs via transfecting reagents offers a better method of transferring a nucleic acid molecule of interest into shrimp eggs without physical damage to the eggs. There have been many reports on the successes of using transfection reagents for transferring desirable genes into mammalian cells and other vertebrates (Boussif et al., "A Versatile Vector for Gene and Oligonucleotide Transfer into Cells in Culture and in vivo Polyethylenimine," *Proc. Natl. Acad. Sci. USA* 92:7297–7301 (1995); Remy et al., "Gene-Transfer with Lipospermines and Polyethylenimines," *Adv. Drug Delivery Rev.* 30:85–95 (1998); Carballada et al., "Transfection of Mouse Eggs and Embryos Using DNA Combined to Cationic Liposomes," *Mol. Reprod. Dev.* 56:360–365 (2000); Horbinski et al., "Polyethylenimine-Mediated Transfection of Cultured Postmitotic Neurons From Rat Sympathic Ganglia and Adult Human Retina," *BMC Neuroscience* 2:1471–2202 (2001); Wall, R. J., "New Gene Transfer Methods," *Theriogenology* 57:189–201 (2002), which are hereby incorporated by reference in their entirety). However, the application of transfecting reagent for gene transfer in shrimp, thus far, is a relatively new approach.

Calderon et al., "Transfection of Shrimp Zygotes Using JetPEI-DNA Complex," In: *Transgenic Animal Research*

Conference IV, Aug. 10–14, 2003, Tahoe City, Calif. (In Press) (2003), which is hereby incorporated by reference in its entirety) recently tested four transfection reagents, Effectene (Qiagen, Valencia, Calif.), SuperFect™ (Qiagen, Valencia, Calif.), Lipofectamine 2000 (GibcoBRL, Bethesda, Md.), and jetPEI™ (Qbiogene, Carlsbad, Calif.), to deliver the expression vector into shrimp zygotes. In that study, shrimp zygotes transfected with DNA in conjunction with the two out of the four reagents, Effectene and jet-PEI™, showed positive expression of the transgene. However, due to the complex procedure required by the transformation of Effectene, jetPEI™ reagent was selected and used in this study.

Figure 3:
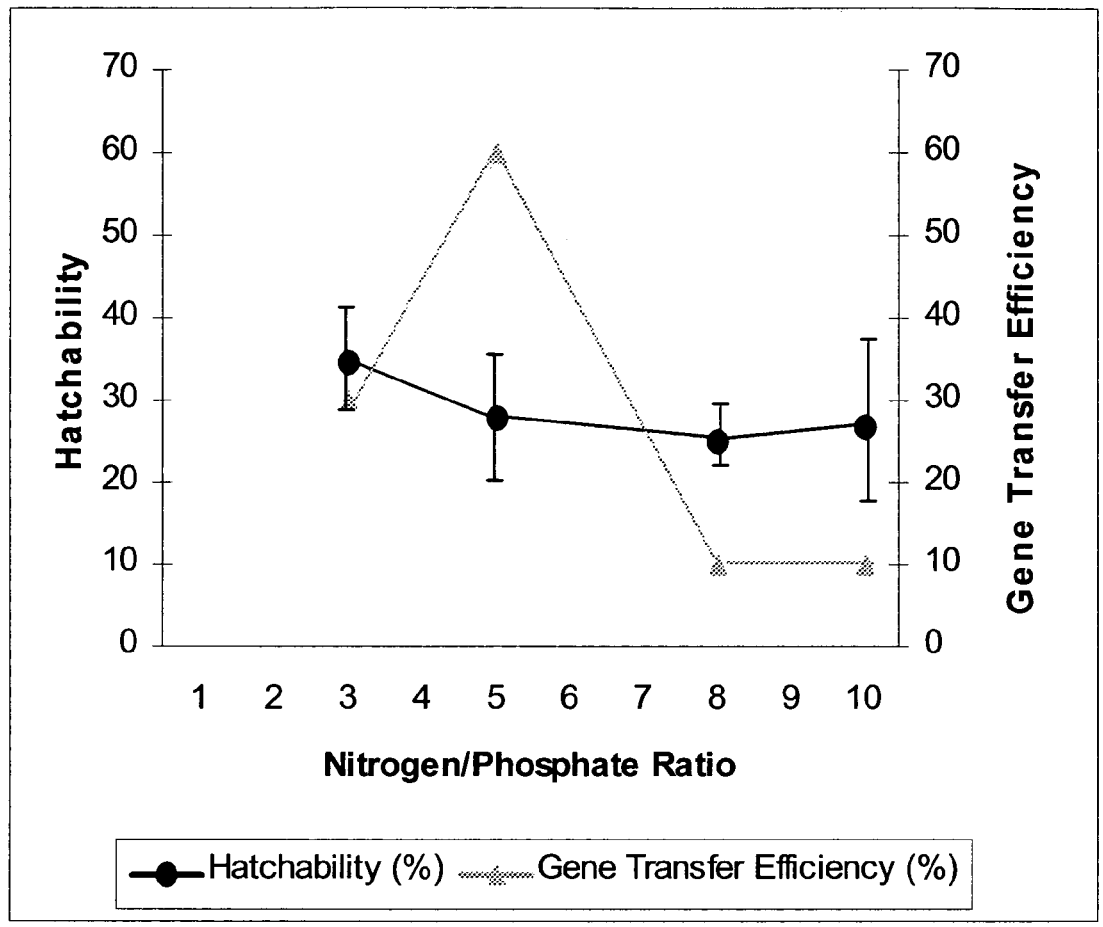
FIG. 3 is a graph showing the effects of Nitrogen to Phosphate (N/P) Ratio on hatchability and gene transfer efficiency of transfection method using jetPEI™. Gene transfer efficiency was determined by genomic PCR on one-week-old putative transgenic shrimp where each value was determined on ten animals.

The transfection reagent jetPEI™ has been reported to have low cellular toxicity in cultured neurons (Horbinski et al., "Polyethylenimine-Mediated Transfection of Cultured Postmitotic Neurons From Rat Sympathic Ganglia and Adult Human Retina," BMC Neuroscience 2:1471–2202 (2001), which is hereby incorporated by reference in its entirety) and is biodegradable (Ahn et al., "Biodegradable Poly(ethylenimine) for Plasmid DNA Delivery," J. Controlled Release 80:273–282 (2002), which is hereby incorporated by reference in its entirety). With jetPEI™, the expression vector pβactP2-TSV-CP(AS) was able to transfer into the shrimp zygotes and achieve a highly efficient gene transfer rate, as shown in FIG. 3. In transfection experiments using jetPEI™, it was found that the high hatching rate of the shrimp eggs does not correlate with a high gene expression rate. It is, therefore, essential to determine the optimal ratio of nitrogen to phosphate (N/P) to be used in the transfection assay. Effective cell entry requires cationic particles. The ionic balance of in vivo jetPEI™ cations and DNA anions should thus be in favor of the former. The N/P ratio is a measure of the ionic balance of the complexes. It refers to the number of nitrogen residues of in vivo jetPEI™ per DNA phosphate. Not every nitrogen atom of PEI being a cation, electroneutrality of in vivo jetPEI™/DNA complexes is reached for N/P=2–3. In practice, the best transfection results are obtained for N/P=5–10. In vivo jetPEI™ is provided as a 150 mM solution (expressed as nitrogen residues) and 1 µg of DNA contains 3 nmoles of anionic phosphate. The amount of in vivo jetPEI™ solution to be mixed with DNA in order to obtain a desired N/P ratio can be calculated using the following formula: (µg of DNA×3)× N/P ratio µl of in vivo jetPEI™ to be used=150 (manufacturer's directions for use of in vivo jetPEI™, which are hereby incorporated by reference in their entirety).

As FIG. 3 shows, despite a high hatching rate shown at a condition of N/P=3, the highest gene expression rate was found at N/P=5. Thus, the condition of N/P=5 was used for most of the transfection experiments.

Figure 4:
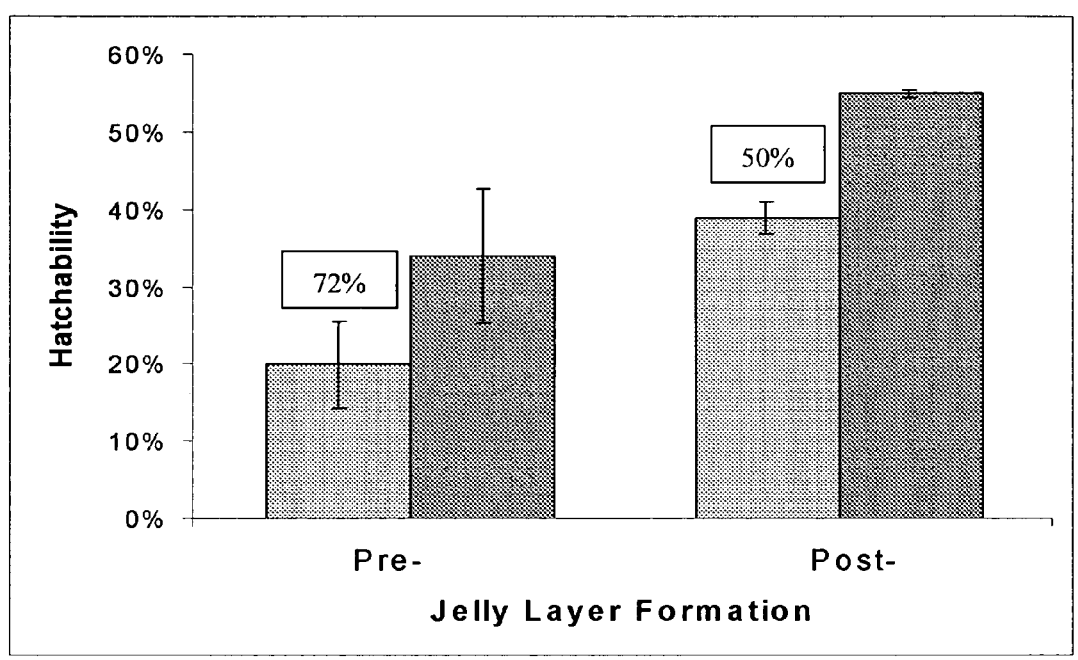
FIG. 4 is a graph showing hatchability following treatment at two zygote developmental stages of the Litopenaeus vannamei. "E" represents experimental shrimp treated with DNA/jetPEI™ complex. "C" represents the control group. The 72% and 50% values represent gene transfer efficiency, which were determined on 18 animals and 10 animals, respectively.

There was a significant difference in gene transfer efficiency when the fertilized shrimp eggs were exposed DNA/jetPEI™ complex at the pre- versus post-jelly layer formation stages. As shown in FIG. 4, shrimp zygotes exposed to pβactP2-TSV-CP (AS) at the pre-jelly layer formation stage resulted in a 20% hatching rate with 72% gene expression efficiency; while shrimp zygotes treated at the post-jelly layer stage resulted in a 42% hatching rate with 50% gene expression efficiency. A high gene transfer rate was observed at the pre-jelly layer stage, however, quantitatively, more transgenic shrimp can be harvested at the post-jelly layer stage due to high hatching rate. Thus, in situations where gene transfer efficiency is critical, for example, the preparation of a breeding line having a transgene of choice, introduction of the nucleic acid into the fertilized egg at the pre-jelly layer formation stage is superior.

Figure 5:
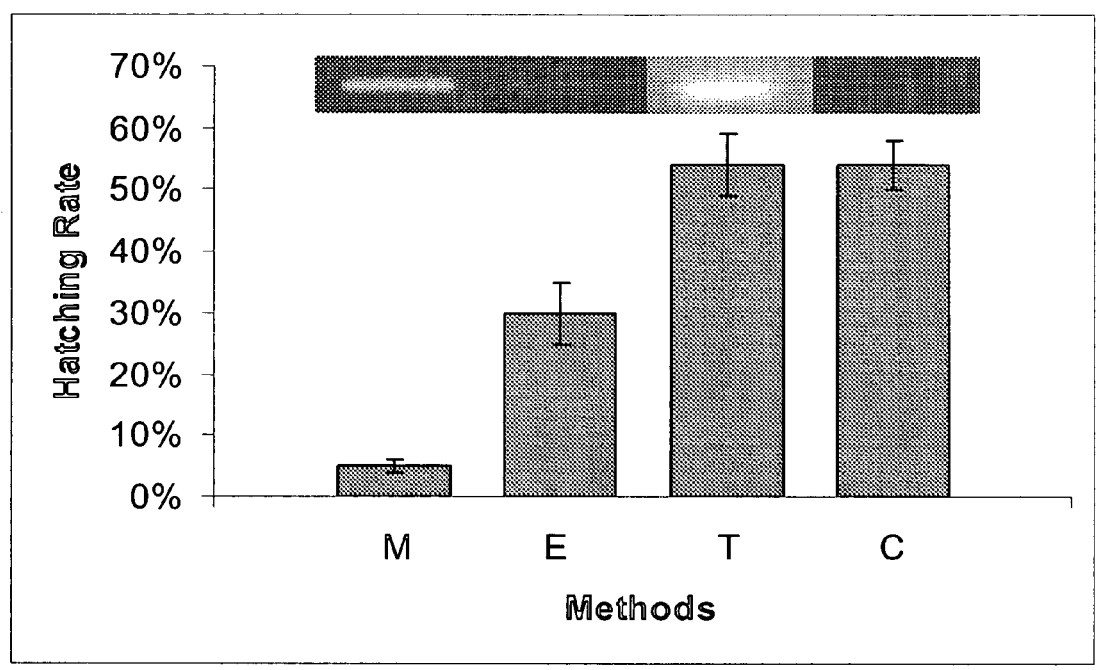
FIG. 5 is a histogram comparing the shrimp hatching rates of the three methods used to deliver nucleic acid to the eggs: microinjection (M), electroporation (E), and transfection with jetPEI™ (T). A shrimp control group is designated (C). Ethidium bromide/agarose gel photos of the target gene expression (302 bp) via RT-PCR (five shrimp per group assayed at the mysis stage) of each corresponding method are shown above the histogram.

Currently, there are no reports of transgenic shrimp being raised to the sexually mature stage. The fact that only 0.4% of shrimp transformed via electroporation survived until the postlarvae (120-day) stage (Tseng et al., "Introducing Foreign DNA into Tiger Shrimp (Penaeus monodon) by Electroporation," Theriogenology 54:1421–1432 (2000), which is hereby incorporated by reference in its entirety), illustrates the difficulty associated with raising transgenic shrimp to maturity. It is speculated that, in addition to the trauma of the electroporation procedure, the low survival rate of the transgenic shrimp could be due to raising the animals in a laboratory setting where conditions such as aquarium space, water quality, temperature, and light exposure are not optimal. In comparison, the use of a linear cationic polyethyleneimine transfection reagent offers a gentle, non-invasive manner of delivering nucleic acids into shrimp zygotes, resulting in relatively higher hatching rate, shown in FIG. 5, as well as gene expression efficiency, shown in Table 2, compared to microinjection and electroporation. While jetPEI™ is similar to electroporation and microinjection in that it can effectively transfect DNA into the shrimp eggs in the presence of the shrimp jelly layer (Calderon et al., "Transfection of Shrimp Zygotes Using JetPEI-DNA Complex," In: Transgenic Animal Research Conference IV, Aug. 10–14, 2003, Tahoe City, Calif., (2003), which is hereby incorporated by reference in its entirety), jetPEI™ has the added advantage of being able to treat a very large number of eggs (20,000–50,000) compared to microinjection (20–50) and electroporation (10,000–15,000) (see Table 1).

Example 7

DNA Transfection without Transfection Reagent

In the one-cell stage, the vector of pβActinP2-TSV-CP, as described above, was successfully delivered into the fertilized shrimp egg in the presence of a transfection reagent, Effectene™ (Qiagen, Valencia, Calif.). Effectene™, a cationic non-liposomal lipid, binds with a specific DNA-condensing enhancer to produce high transfection efficiencies in the shrimp system. Procedures of transfection optimization using Effectene™ were followed according to the description in the Handbook of Transfection Reagent (Qiagen, Valencia, Calif.) and were modified as described by Calderon et al., "Selection of Transfection Reagents for Foreign DNA Delivery into the Pacific White Shrimp Litopenaeus vannamei Embryos," World Aquaculture Conference, Salvador, Brazil (2003), which is hereby incorporated by reference in its entirety. Briefly, each transfection reaction was carried out in a 35×10 mm polystyrene sterile petri dish with a solution containing suitable amount of plasmid DNA, buffer E.C. (Qiagen, Valencia, Calif.), enhancer, and Effectene™. Control samples were run in parallel to the experimental ones. Control samples contain only plasmid DNA in TE buffer. Prior to adding 800 µl fertilized shrimp egg, the reaction mixture was incubated at room temperature for 15 min with gentle shaking, followed by adding 400 µl of sterile sea water (total reaction volume: 488 µl). The incubation period continued for another 20 min with shrimp eggs in the mixture. At the end of incubation, the reaction mixture was transferred to a one-liter beaker with sterile aerated sea water at 28° C. The number of hatched eggs was counted and recorded 24 hours after spawning, and live nauplii were raised in the beaker until harvesting for gene expression assay using reverse transcription-polymerase chain reaction (Venzon et al., "Effect of Temperature on Taura Syndrome Virus Challenge of Juvenile Litopenaeus vannamei," In:

Federation of American Societies for Experimental Biology, Section of American Society for Investigative Pathology, New Orleans, La., USA, p. A967 (2002), which is hereby incorporated by reference in its entirety).

As shown in FIG. 6, target gene expression was detected when the ratio (w/w) of DNA to Effectene™ was between 0.02 to 0.05 and the vector DNA concentration was 0.4 μg/ml of medium. In addition, it was found that plasmid DNA (0.5–2.0 μg/ul of pβActP2-TSV-CP) alone can directly diffuse into the egg embryo at the naked stage (about 7–12 min post-spawning) without a transfection reagent. This finding, shown in FIG. 6, suggests that at the naked, i.e., pre-jelly coat stage of the shrimp embryo, foreign DNA can enter the egg in the absence of transfection reagent. The experiment was repeated using additional commercially available transfection reagents. The results, shown in FIG. 7, demonstrate that DNA alone is more effective than DNA combined with a transformation reagent when the egg is exposed to the DNA during the early phase of jelly coat formation. That effect may be also dependent upon DNA concentration. The success with plasmid DNA alone (no vector) is indicative that naked DNA, which possesses a charge, can be introduced to a fertilized egg during the one-cell stage without being associated with a vector. Naked DNA, associated only with the 5' and 3' regulatory sequences requisite for expression, and having the specific advantages described herein above, would be useful in the present invention for delivery of a desired gene to egg with minimal damage and high expression efficiency.

Example 8

Detection of Target Gene Expression

Total RNA isolated from the microinjected, electroporated, and jetPEI™/DNA transfected shrimp was used as a template in RT-PCR reaction to detect the expression of the TSV-CP target gene. TSV-CP gene specific primer pair (primer 1 (SEQ ID NO: 1): 5'-CTTAATTAATGCCTGCTAACCC-3'; primer 2: (SEQ ID NO: 2) 5'-ATTGATGTCTGCTTAGCATTCA-3') was used in the RT-PCR reaction. A second round PCR reaction was performed using 1 μl of the RT-PCR product as a template and the TSV-CP nested gene specific primer pair (primer 3: (SEQ ID NO: 3): 5'-TGATACAACAACCAGTGGAGGAC-3'; primer 4: (SEQ ID NO: 4): 5'-TGTCATCAGGTAGGGAAATTTC-3'). The primer sequences were based on the published sequence of the TSV-CP (GenBank Accession No. AF277378), which is hereby incorporated by reference in its entirety. An expected 302-bp DNA fragment was generated from the shrimp samples microinjected, electroporated, or jetPEI™ transfected with pβact-TSV-CP(AS), indicating expression of the TSV-CP target gene by the shrimp. The RT-PCR procedure were followed as described by Sun et al., "Spatial Expression of the Molt-Inhibiting Hormone-Like Gene in the White Shrimp *Penaeus vannamei*," *Aquaculture* 135:239–243 (1995), which is hereby incorporated by reference in its entirety.

Genomic DNA was isolated using the Puregene DNA isolation Kit (Gentra Systems, Minneapolis, Minn.) from the microinjected, electroporated, or jetPEI™/DNA transfected shrimp and used as a template for the PCR assay. The expected DNA band of either 493 bp (when primer 1 and primer 2 were used) or 302 bp (when primer 3 and primer 4 were used) was revealed from ethidium bromide/agarose gel electrophoresis, indicating the presence of the TSV-CP target gene in the shrimp body.

Among the methods tested, the polyethyleneimine transfecting reagent jetPEI™ seems to be the most efficient method for introducing nucleic acids into shrimp eggs due to its simple procedures and high hatching rate, gene transfer efficiency, and survival rates. Also, this method has the capacity to perform large-scale shrimp egg transfections. In contrast, microinjected and electroporated shrimp have been shown to have short life-spans and exhibited difficulties in raising the animals to the sexually mature stage.

When stable transformation of a transgenic animal is achieved, the gene is incorporated into the organism's genome, and the gene is, therefore, heritable. Putative transgenic shrimp transfected with jetPEI™ are currently in the maturation process in the inventor's laboratory. It is of interest to raise the animals to their sexually mature stage for the purpose of studying whether the introduced foreign gene can be inherited in the next generation.

The in vivo gene delivery described herein to deliver a desired target nucleic acid molecule into the shrimp egg in a critical stage during embryonic development of the shrimp proves to be a simple and highly efficient method for transformation of DNA. This nucleic acid transfer system using jetPEI™ (Qbiogene, Carlsbad, Calif.), Effectene™ (Qiagen, Valencia, Calif.) (or other suitable transfection reagents) or using DNA alone, with or without a vector, can be employed to allow transient and stable transfection of a variety of crustacean organisms with minimal physical damage to the embryos in comparison to other gene delivering systems such as microinjection, particle gun bombardment, and electroporation. Furthermore, this gene delivery system could be used in a large scale production of transgenic shrimp or other transgenic animal, including, but not limited to, crustaceans and marine and freshwater fish.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A method of producing a transgenic shrimp, said method comprising:
   providing a fertilized shrimp egg prior to its full formation of a protective layer;
   providing a nucleic acid molecule; and
   combining the nucleic acid molecule and the fertilized egg under conditions effective to allow the nucleic acid molecule to be delivered into the egg without removing the protective layer, thereby yielding a transgenic shrimp having the nucleic acid molecule integrated into the genomic DNA of said transgenic shrimp.

2. The method according to claim 1, wherein the nucleic acid molecule is heterologous to the transgenic shrimp.

3. The method according to claim 1, wherein the nucleic acid molecule is homologous to the transgenic shrimp.

4. The method according to claim 1, wherein the nucleic acid molecule is in an expression vector.

5. The method according to claim 4, wherein the expression vector is a linear vector.

6. The method according to claim 4, wherein the expression vector is a circular vector.

7. The method according to claim 4, wherein the expression vector comprises a label.

8. The method according to claim 7, wherein the label is selected from the group consisting of a radio-active label, a fluorescent label, a chemiluminescent label, and a biotinylated label.

9. The method according to claim 1, wherein the nucleic acid molecule comprises a label.

10. The method according to claim 9, wherein the label is selected from the group consisting of a radio-active label, a fluorescent label, a chemiluminescent label, and a biotinylated label.

11. The method according to claim 1, wherein said combining comprises:
    combining a transfection reagent with the nucleic acid molecule and the fertilized egg.

12. The method according to claim 11, wherein the transfection reagent is selected from the group consisting of a cationic lipid reagent, a liposomal cationic lipid reagent, a cationic non-liposomal lipid reagent, an activated dendrimer reagent, and a cationic polyethyleneimine reagent.

13. The method according to claim 12, wherein the transfection reagent is a cationic polyethyleneimine.

14. The method according to claim 12, wherein the transfection reagent is a linear cationic polyethyleneimine reagent.

* * * * *